(12) United States Patent
Larzon et al.

(10) Patent No.: US 10,159,474 B2
(45) Date of Patent: *Dec. 25, 2018

(54) VASCULAR CLOSURE DEVICE

(71) Applicant: M-V Arterica AB, Göteborg (SE)

(72) Inventors: Thomas Larzon, Örebro (SE); Robert G. Whirley, Santa Rosa, CA (US); Daniel Karlsson, Torslanda (SE); Henrik Nyman, Olofstorp (SE); Joseph Humphrey, Santa Rosa, CA (US); Cecilia Larzon, Göteborg (SE)

(73) Assignee: M-V ARTERICA AB, Göteborg (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/611,665

(22) Filed: Jun. 1, 2017

(65) Prior Publication Data

US 2017/0265848 A1   Sep. 21, 2017

Related U.S. Application Data

(63) Continuation of application No. 15/291,991, filed on Oct. 12, 2016, which is a continuation of application No. 15/277,542, filed on Sep. 27, 2016.

(30) Foreign Application Priority Data

Sep. 28, 2015 (SE) .................................. 1551238
Nov. 6, 2015 (SE) .................................. 1551441

(51) Int. Cl.
*A61B 17/00* (2006.01)
*A61B 17/04* (2006.01)
(Continued)

(52) U.S. Cl.
CPC ...... *A61B 17/0057* (2013.01); *A61B 17/0401* (2013.01); *A61B 17/0469* (2013.01); *A61B 17/0487* (2013.01); *A61B 17/06166* (2013.01); *A61M 25/09* (2013.01); *A61B 2017/00004* (2013.01); *A61B 2017/00663* (2013.01);
(Continued)

(58) Field of Classification Search
None
See application file for complete search history.

(56) References Cited

U.S. PATENT DOCUMENTS 5,364,408 A   11/1994   Gordon
5,417,699 A   5/1995   Klein et al.
(Continued)

FOREIGN PATENT DOCUMENTS

EP   2095774   9/2009
WO   WO 97/03613   2/1997

OTHER PUBLICATIONS

Bountouris et al., "Endovascular aneurysm repair with Fascia suture technique: short and mid-term results," Int Angiol, Epub Nov. 10, 2015.
(Continued)

*Primary Examiner* — Shaun L David
(74) *Attorney, Agent, or Firm* — Schmeiser, Olsen & Watts LLP

(57) ABSTRACT

The present disclosure relates to a vascular closure device adapted for use in closing a puncture in a blood vessel after e.g. a percutaneous interventional procedure. The disclosure also relates to a method for vascular closure using such a vascular closure device.

19 Claims, 19 Drawing Sheets

(51) Int. Cl.
*A61B 17/06* (2006.01)
*A61M 25/09* (2006.01)

(52) U.S. Cl.
CPC .............. *A61B 2017/00676* (2013.01); *A61B 2017/00778* (2013.01); *A61B 2017/0409* (2013.01); *A61B 2017/0417* (2013.01); *A61B 2017/0427* (2013.01); *A61B 2017/0464* (2013.01); *A61B 2017/0472* (2013.01); *A61B 2017/0488* (2013.01)

(56) References Cited

U.S. PATENT DOCUMENTS

| | | | |
|---|---|---|---|
| 5,700,273 | A | 12/1997 | Buelna et al. |
| 5,716,375 | A | 2/1998 | Fowler |
| 5,868,762 | A | 2/1999 | Cragg et al. |
| 6,059,800 | A | 5/2000 | Hart et al. |
| 6,231,561 | B1 | 5/2001 | Frazier et al. |
| 6,626,918 | B1 | 9/2003 | Ginn et al. |
| 8,617,204 | B2 | 12/2013 | Khosravi et al. |
| 8,821,532 | B2 | 9/2014 | Schaeffer |
| 8,920,442 | B2 | 12/2014 | Sibbitt, Jr. et al. |
| 2002/0026208 | A1 | 2/2002 | Roe et al. |
| 2002/0045908 | A1 | 4/2002 | Nobles et al. |
| 2005/0149066 | A1 | 7/2005 | Stafford |
| 2006/0069397 | A1 | 3/2006 | Nobles et al. |
| 2006/0142784 | A1 | 6/2006 | Kontos |
| 2007/0203506 | A1 | 8/2007 | Sibbitt, Jr. et al. |
| 2008/0177288 | A1 | 7/2008 | Carlson |
| 2009/0254119 | A1 | 10/2009 | Sibbitt, Jr. et al. |
| 2009/0264922 | A1* | 10/2009 | Mas .................. A61B 17/0057 606/216 |
| 2012/0290001 | A1 | 11/2012 | Uchida et al. |
| 2013/0231701 | A1 | 9/2013 | Voss et al. |
| 2015/0066055 | A1 | 3/2015 | Sibbitt, Jr. et al. |
| 2015/0105805 | A1 | 4/2015 | Forston |
| 2017/0086804 | A1 | 3/2017 | Larzon et al. |
| 2017/0086807 | A1 | 3/2017 | Larzon et al. |

OTHER PUBLICATIONS

Fisher, "The Fascia Suture Technique: This Late Bloomer Could Become a Winner," J. Endovasc Ther, 2012, 19:397-399.

Freitas et al., "The use of closure devices in peripheral endovascular interventions: The Leipzig real-world report," Journal of the American College of Cardiology, TCT Abstracts/Vascular Access and Intervention—Femoral (includes closure devices) Abstract TCT-842, p. B245, Saturday, Sep. 13, 2014, 5:00 PM-7:00 PM.

Harrison et al., "Fascial Closure Following Percutaneous Endovascular Aneurysm Repair," Eur J Vasc Endovasc Surg (2011) 41, 346-349.

Larzon et al., "Editor's Choice—A Randomized Controlled Trial of the Fascia Suture Technique Compared with a Suture-mediated Closure Device for Femoral Arterial Closure after Endovascular Aortic Repair," Eur J Vasc Endovasc Surg (Feb. 2015) 49, 166-173.

Larzon et al., "Fascia Suturing of Large Access Sites After Endovascular Treatment of Aortic Aneurysms and Dissections," J Endovasc Ther, 2006, 13:152-157.

Lee et al., "Midterm outcomes of femoral arteries after percutaneous endovascular aortic repair using the Preclose technique," J Vasc Surg, 2008: 47:919-923.

Mathisen et al., "Complication Rate of the Fascia Closure Technique in Endovascular Aneurysm Repair," J Endovasc Ther 2012; 19:392-396.

Montan et al., "Short- and Midterm Results of the Fascia Suture Technique for Closure of Femoral Artery Access Sites After Endovascular Aneurysm Repair," J Endovasc Ther, 2011; 18:789-796.

Nelson, "Closure and Arterial Acces Conundrums" Presentaion, Saturday Jun. 7, 2014, Society for Vascular Surgery, 2014 Vascular Annual Meeting, Boston, Jun. 5-7.

Wanhainen, A., "Invited Commentary, Commentary on 'A Randomized Controlled Trial of the Fascia Suture Technique Compared with a Suture-mediated Closure Device for Femoral Arterial Closure After Endovascular Aortic Repair'" Eur J Vasc Endovasc Surg (Feb. 2015) 49, 174-174.

International Search Report and Written Opinion dated Jan. 31, 2017 in International Application No. PCT/IB2016/001498 filed: Sep. 27, 2016.

Non Final Office Action dated Dec. 15, 2016 in U.S. Appl. No. 15/291,991, filed Oct. 12, 2016, published as US-2017/0086807 on Mar. 30, 2017.

Notice of Allowance dated May 12, 2017 in U.S. Appl. No. 15/291,991, filed Oct. 12, 2016, published as US-2017/0086807 on Mar. 30, 2017.

Non-Final Office Action dated Aug. 30, 2018 in U.S. Appl. No. 15/277,542 filed Sep. 27, 2016, published as: US 2017-0086804 on Mar. 30, 2017.

* cited by examiner

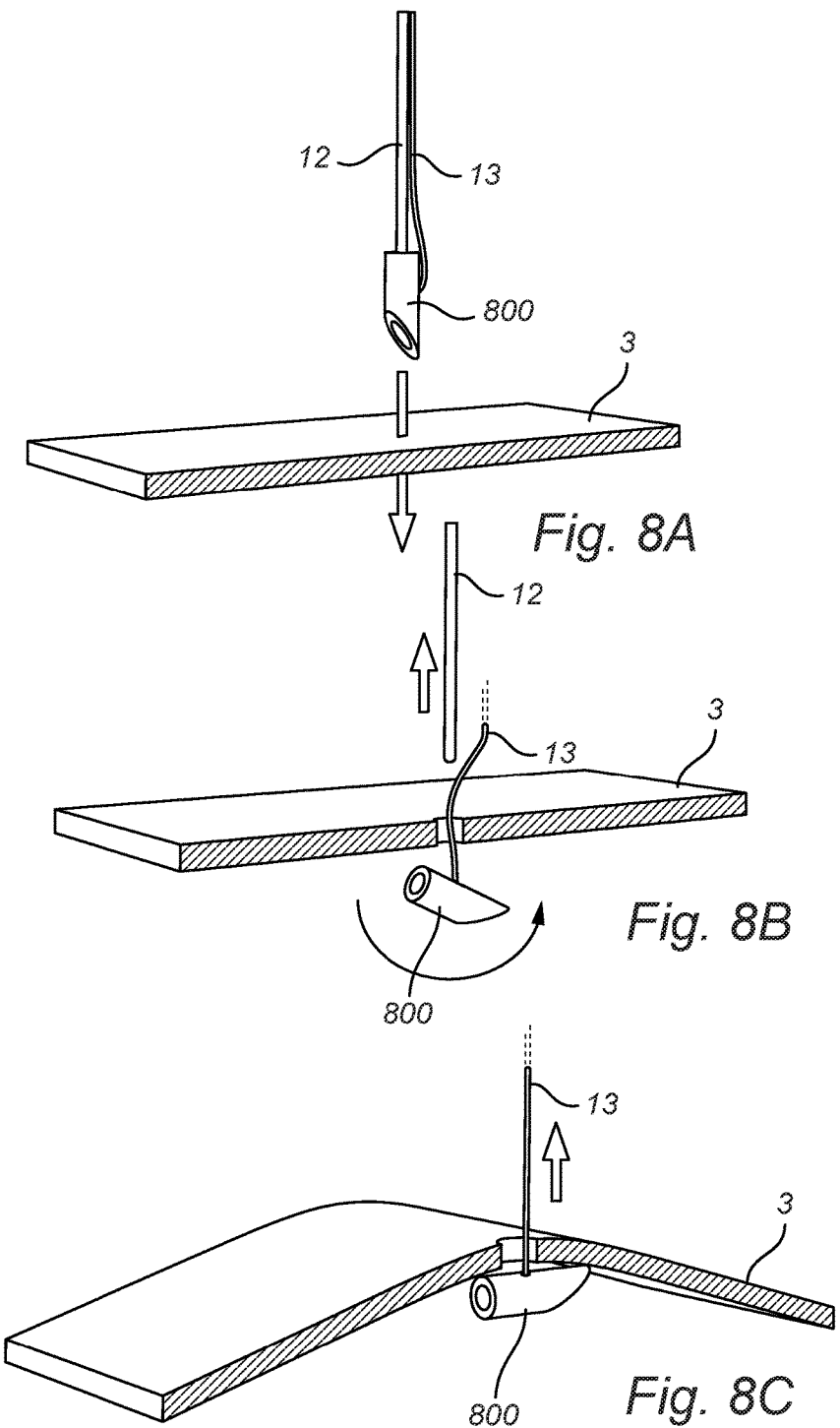

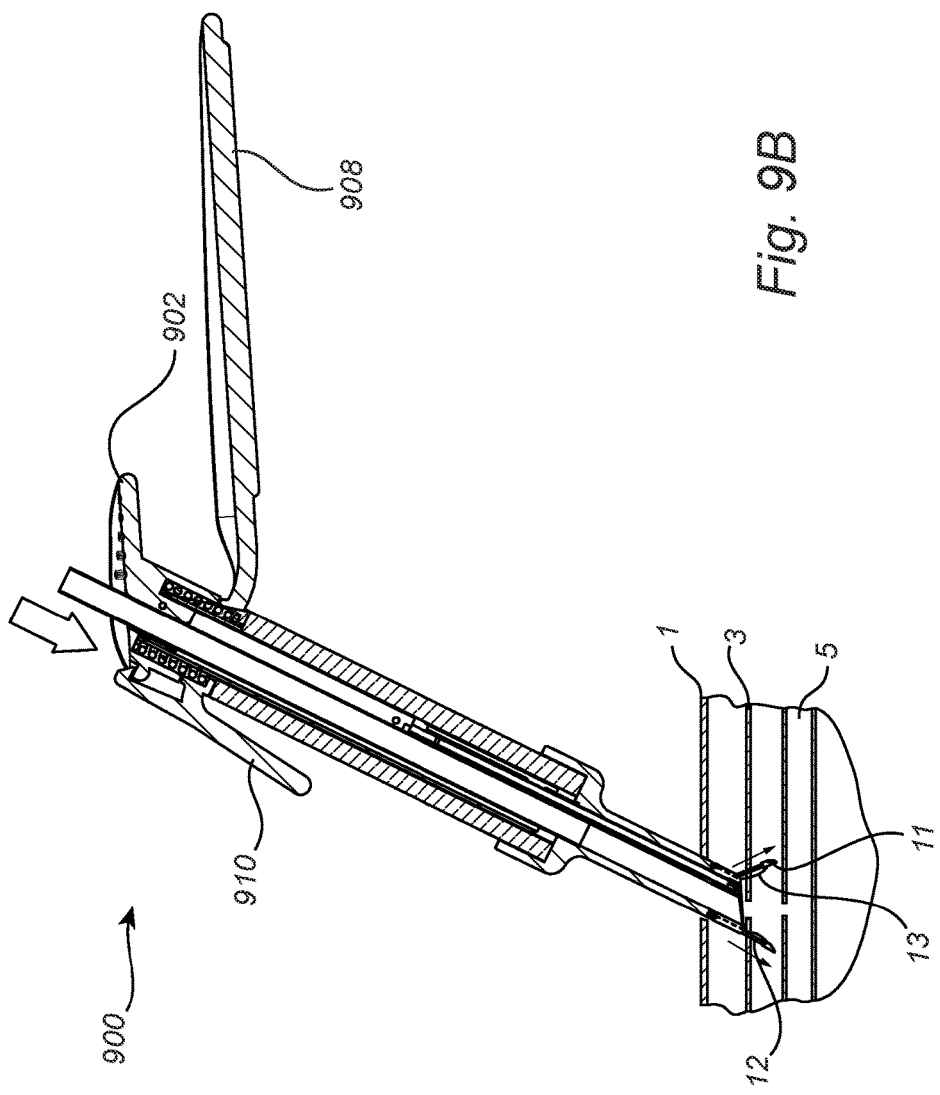

VASCULAR CLOSURE DEVICE

RELATED PATENT APPLICATIONS

This patent application is a continuation of U.S. patent application Ser. No. 15/291,991, filed Oct. 12, 2016, naming Thomas Larzon, Robert G. Whirley, Daniel Karlsson, Henrik Nyman, Joseph Humphrey and Cecilia Larzon as inventors, entitled VASCULAR CLOSURE DEVICE, which is a continuation of U.S. patent application Ser. No. 15/277,542, filed Sep. 27, 2016, naming Thomas Larzon, Robert G. Whirley, Daniel Karlsson, Henrik Nyman, Joseph Humphrey and Cecilia Larzon as inventors, entitled VASCULAR CLOSURE DEVICE, which claims the benefit of Swedish Patent Application No. 1551238-7, filed Sep. 28, 2015, naming Thomas Larzon as inventor and entitled VASCULAR CLOSURE DEVICE, and Swedish Patent Application No. 1551441-7, filed Nov. 6, 2015, naming Thomas Larzon as inventor, entitled VASCULAR CLOSURE DEVICE, all of which are incorporated by reference herein in their entirety, including all text and drawings.

TECHNICAL FIELD

The present disclosure relates to a vascular closure device adapted for use in closing a puncture in the artery after e.g. a percutaneous interventional procedure. The disclosure also relates to a method for vascular closure using such a vascular closure device.

BACKGROUND OF THE DISCLOSURE

In most cardiovascular procedures, a catheter is inserted into an artery, such as the femoral artery, either directly or through a percutaneous vascular access. The catheter may be inserted, typically over a guidewire, directly into an artery (a "bareback" procedure), or the catheter may be inserted through a vascular introducer. When the procedure is complete, the physician removes the catheter and then removes the introducer from the vessel (if one was used). The physician then must prevent or limit the amount of blood that leaks through the vascular access. Physicians currently use a number of methods to close the vascular access, such as localized external compression, suture-mediated closure devices, plugs, gels, foams and similar materials.

However, such closure procedures may be time consuming, and may consume a significant portion of the time of the procedure. In addition, existing methods are associated with complications such as hematoma or thromboses. Still further, some of such procedures, particularly suture-mediated closure devices, are known to have high failure rates in the presence of common vascular disease such as atherosclerosis and calcification.

EP 2095774 B1 tries to overcome the above-mentioned problems by introducing a semi-automated closure apparatus. The suggested closure apparatus is provided for delivering a closure element into engagement with tissue adjacent an opening into a body lumen. The apparatus includes a sheath including a lumen extending between its proximal and distal ends, and a locator member disposed within the sheath, the locator member having a distal portion extending distally beyond the distal end of the sheath. One or more positioning elements are provided on the distal portion of the locator member, the positioning elements being selectively expandable between a substantially axial collapsed configuration and a substantially transverse expanded configuration.

Even though EP 2095774 B1 provides some relief for the patient by reducing the time necessary for performing a vascular closure, there appears to be room for further improvement in regards to rapid vascular closure, specifically in regards to a device that is easy to use.

SUMMARY

In view of above-mentioned and other drawbacks of the prior art, there is in accordance to the first aspect of the present disclosure therefore provided a vascular closure device for closing a passage through tissue proximate to a blood vessel, the vascular closure device comprising an elongated housing having a proximal end and a distal end, the distal end adapted to be proximate the tissue, a first and a second engagement member releasably arranged with the elongated housing, a deployment member arranged with the elongated housing and adapted to deploy the first and the second engagement member at a distance from each other in engaged contact with said tissue, without engaging a wall portion of the blood vessel, and a retraction member arranged with the elongated housing and adapted to reduce the distance between the first and the second engagement member to close said passage.

According to the present disclosure, the vascular closure device may be used percutaneously at a vascular access site used for a diagnostic or therapeutic intervention. A vascular access site may in some embodiments correspond to the expression "the passage through tissue proximate to a blood vessel". Engagement members may then be placed and released through the vascular closure device and may attach to the tissue proximate to the blood vessel, however without engaging a wall portion of the blood vessel. The engagement members are subsequently released out from the vascular closure device using the deployment member, for example using pusher rods arranged in independent lumens comprised with the vascular closure device. In an embodiment, a pusher assembly may for example be arranged in a common lumen that simultaneously deploys all engagement members, through a spring-loaded mechanism or by means of similar functionality. The engagement members may preferably be connected with an elongate flexible tension element such as a suture. The suture may be routed through each of the engagement members in sequence, or individually connected to each engagement member. The tissue in proximity to the blood vessel may then be pulled together with the suture(s) connected to the engagement members. When pulled together, the distance between the initial positions where the engagement members have been positioned to engage with the tissue will be reduced, thereby closing the passage, e.g. the mentioned vascular access site. The tightening accordingly creates a tissue lock thereby closing the passage in the tissue proximate to the blood vessel and indirectly closing the passage in the blood vessel/artery.

Advantages with the present disclosure include the possibility of closing large passages, such as a large bore access site, post-procedure, and that no preparation of the access site for percutaneous closure is necessary prior to the time of closure, being of high importance e.g. during acute cases. The present disclosure is however not limited to large bore holes, also small passages/holes can be closed with the present vascular closure device.

In addition to the above, it should specifically be understood that the blood vessel is not engaged directly and thus not included when closing the passage in the tissue proximate the blood vessel, rather, only the tissue proximate to the blood vessel is used for closing the passage. This may typically avoid complications involved with diseased vessels, such as dissection of the intimal layer that can occur and that might cause thrombosis, or such calcified plaques may be present and prevent penetration of the arterial wall. Furthermore, the proposed vascular closure device replaces an established invasive, manual surgical procedure with an automatized, minimally invasive, and easy to learn closure method.

The terms "proximal" and "distal" are used herein with reference to a clinician manipulating the vascular closure device. The term "proximal end" referring to the portion closest to the clinician and the term "distal end" referring to the portion located away from the clinician. It will be further appreciated that, for convenience and clarity, spatial terms such as "vertical", "horizontal", "up", and "down" may be used herein with respect to the drawings. However, the vascular closure device may be used in many orientations and positions, and these terms are not intended to be limiting and/or absolute.

It is in some embodiments possible to adapt the engagement member to mechanically engage (or anchor into) the tissue, possibly at a predetermined distance from the distal end of the vascular closure device. The predetermined distance may in one embodiment be as small as only a few millimeters.

In one embodiment, the first and the second engagement members are adapted to engage with a fascia membrane of said tissue. The fascia membrane is made up of fibrous connective tissue containing closely packed bundles of collagen fibers oriented in a wavy pattern. The fascia membrane is consequently flexible and able to resist great unidirectional tension forces until the wavy pattern of fibers has been straightened out by the pulling force. Adapting the vascular closure device such that the first and the second engagement members are adapted to engage with the fascia membrane of said tissue is thus, in some embodiments, considered suitable for further enhancing the closure of the passage to the blood vessel. The structure of the fascia membrane may additionally allow for the distance reduction, as mentioned above, to be performed without risking that the first and the second engagement members dislocate/disengage from the tissue.

In an embodiment of the present disclosure, the vascular closure device further comprises an anvil member to be used for determining a location of the anterior wall of the blood vessel/artery, and thereby to be used for providing a reference point in relation to the blood vessel. By means of such an implementation, it may be possible to allow the first and the second engagement members to successfully engage with said tissue at a predetermined distance from anvil member. In a possible embodiment, the distal end of the elongated housing may be positioned e.g. a few millimeters above the fascia membrane, typically not in contact with the fascia membrane or the wall position of the blood vessel.

In addition to providing a reference point to the engagement members, the anvil member may additionally be used for controlling bleeding during the procedure. However, it should be understood that it of course may be possible to include a further hemostasis member adapted to block blood flow through the passage in the fascia, blood vessel or both, where the hemostasis member is positioned within the blood vessel prior to deploying the first and the second engagement member.

As mentioned above, the anvil member may provide an orientation in relation to the blood vessel, possibly in a two-dimensional orientation (x-y) in relation to the blood vessel. This may further allow for the first and the second engagement member to mechanically capture or otherwise be secured to the tissue with a predetermined pattern in relation to the blood vessel.

The anvil member may for example comprise one of a balloon, a deployable disk, a deployable positioning feature or an anchoring plate, depending on the selected implementation of the vascular closure device. Similar anvil members are of course possible. In addition, it is in accordance with the present disclosure possible to remove the anvil member from blood vessel in completing the procedure involving the vascular closure device, leaving nothing behind in the artery. The anvil member may for example be arranged to form part of the elongated housing.

As an alternative to using the anvil member for providing a reference point in relation to the blood vessel, it could be possible to adapt the vascular closure device to instead comprise a small port on the distal end of the device, which communicates with a lumen that extends an external port near the proximal end of the device. The operator of the vascular closure device may then determine the reference point by inserting the vascular closure device until blood is seen coming from the proximal port, thereby indicating that the distal port is just inside the blood vessel and blood pressure is forcing blood through the vascular closure device.

The vascular closure device may additionally further comprise a device-positioning member to be aligned with a longitudinal axis of the blood vessel prior to deploying the first and the second engagement member. Such a device positioning member may for example be implemented using an extendable portion of the housing, where the device positioning member is to be aligned e.g. with a limb (e.g. leg or arm) where the passage is located.

As mentioned above, it is possible to allow a suture to be connected to the first and the second engagement member, wherein the retraction member is adapted to retract the suture to reduce the distance between the first and the second engagement member. A single suture may be used connect to all of the engagement members, or alternatively the suture and a corresponding further suture may be individually connected to the first and the second engagement member, respectively. It should be understood that it may be possible, and within the scope of the present disclosure, to include e.g. a third and a fourth (or even further) engagement members, where a single or a plurality of sutures may be connected to the engagement members in a similar manner as mentioned. Alternatively, a separate suture may be attached to each engagement member and routed into a lumen through the distal aspect of the device such that applying tension to the sutures serves to pull the fascia attachments toward the vascular closure device, reduce the distance between the engagement members and thereby close the passage.

In some embodiments, it may be suitable to form the suture/sutures from a biodegradable or bio-absorbable material, such as a bio-absorbable polymer. In addition, also the engagement member may be formed from a similar biodegradable or bio-absorbable material. This will allow post handling of the closure site to be simplified as no further engagement is needed for removing the engagement members/suture(s).

In an embodiment of the present disclosure, the vascular closure device is further adapted to comprise a suture restraint or a locking member arranged with the elongated housing and adapted to maintain the suture in a retracted state, thereby creating the above mentioned tissue lock. In addition, the locking member may be formed from a similar biodegradable and bio-absorbable material. The locking arrangement may for example be formed from a wire or similar encircling a bundle of collected sutures, in case of using individual sutures for each of the engagement members or in case of a suture looped by the plurality of engagement members, thus forming two end portions of the suture to be bundled together. In addition, in one embodiment it may be possible to form the locking member from a preloaded coil arranged to clench and secure the tightened suture relative to each other in the retracted state.

Accordingly, in the case of providing individual sutures to each of the engagement members (or using the mentioned two end portions of a looped single suture), the plurality of sutures (or suture end portions) may be routed into the center of a lumen that protrudes distally from the main housing of the vascular closure device. The locking member, such as the suture retention coil, may in such an embodiment initially be placed over the outer diameter of this lumen, and to be preloaded or pre-stretched such that the coil collapses to a smaller diameter when it is displaced off the distal tip of the lumen and contracts onto the sutures and thereby serves to prevent relative motion of the two or more sutures. The suture retention coil may be deployed, at the appropriate time, by distally sliding another tube that is external to the lumen on which the suture retention coil is preloaded such that the outer tube pushes the coil off the inner tube and enables it to contract onto the plurality of sutures. The suture retention coil may consist of two or more coil windings; in another embodiment three to four coil windings, in a helical configuration. In a possible embodiment, the wire used to construct the coil may not be of round cross section and may have edges or angles to increase friction with the suture.

Furthermore, the engagement member (such as the first and the second and further engagement members) may be formed in a structure corresponding to one of a barb, a hook, a needle, an anchor and a spear to mechanically capture the tissue, possibly including the fascia membrane, to provide a suitable connection point for allowing the retraction member to subsequently reduce the distance between the engagement members.

The engagement members may alternatively comprise an anchor (or be formed in a manner providing a corresponding functionality), where the anchor may be arranged as a flexible structure. Still further, the anchor may be adapted to rotate, pivot or expand once in engaged connection with said tissue, possibly including the fascia membrane, thereby further enhancing mechanical capturing of such an anchor within the tissue in some cases. In an alternative embodiment, it is possible to adapt the anchor to expand after being pushed into the fascia membrane.

For example, the anchor may be adapted to have an umbrella like shape in the collapsed position as it passes through the fascia membrane, and then either a stored spring force or tension on the suture could cause it to expand into a reverse-conical configuration, similar to an open umbrella, so that it presents much more surface area to the fascia than did the anchor in the original configuration, and thereby provides increased retention strength in the fascia. In addition, the engagement members may also comprise a hypotube section having an inclined end portion, as will be further discussed below in relation to the detailed description of the present disclosure.

According to a further aspect of the present disclosure, there is provided a method of closing a passage through tissue communicating with a blood vessel, the method comprising providing a vascular closure device, the vascular closure device comprising an elongated housing having a proximal end and a distal end, a first and a second engagement member releasably arranged with the elongated housing, a deployment member arranged with the elongated housing, and a retraction member arranged with the elongated housing. Once provided, the distal end of the vascular closure device is positioned proximate to the tissue, deploying, using the deployment member, the first and the second engagement member from the vascular closure device to engage with said tissue at a distance from each other, without engaging a wall portion of the blood vessel, applying a predetermined retraction force, using the retraction member, to reduce the distance between the first and the second engagement member to close said passage. This aspect of the present disclosure provides similar advantages as discussed above in relation to the previous aspect of the present disclosure.

Some embodiments of a vascular closure device for treating a passage in a blood vessel by closing a passage through tissue proximate to a blood vessel, may include an elongated housing having a proximal end, a distal end, and a distal section and a plurality of engagement members which are each adapted to be secured to tissue upon deployment into tissue. A plurality of deployment members may be adapted to extend from the distal section of the elongated housing in a distal and radially outward direction, with each of the deployment members being adapted to deploy at least one of the engagement members into the tissue proximate to the blood vessel such that the engagement members are secured to the tissue proximate to the blood vessel and disposed at a distance from each other in engaged contact with said tissue, without engaging a wall portion of the blood vessel. Each of a plurality of elongate flexible tension elements may be secured to at least one engagement member. A retraction member is coupled in operative arrangement with the tension elements and adapted to apply axial tension to the tension elements and reduce the distance between the engagement members to a radially retracted state to close the passage in the tissue proximate to the blood vessel.

Further features of, and advantages with, the present disclosure will become apparent when studying the appended claims and the following description. The skilled addressee will realize that different features of the present disclosure may be combined to create embodiments other than those described in the following, without departing from the scope of the present disclosure.

BRIEF DESCRIPTION OF THE DRAWINGS

The various aspects of the disclosure, including its particular features and advantages, will be readily understood from the following detailed description and the accompanying drawings, in which:

FIGS. 8A-8C illustrate the operation of a further engagement member embodiment, provided as a cut hypotube;

FIGS. 9A-9C illustrate a cross section of a further embodiment of a vascular closure.

DETAILED DESCRIPTION

Figure 1:
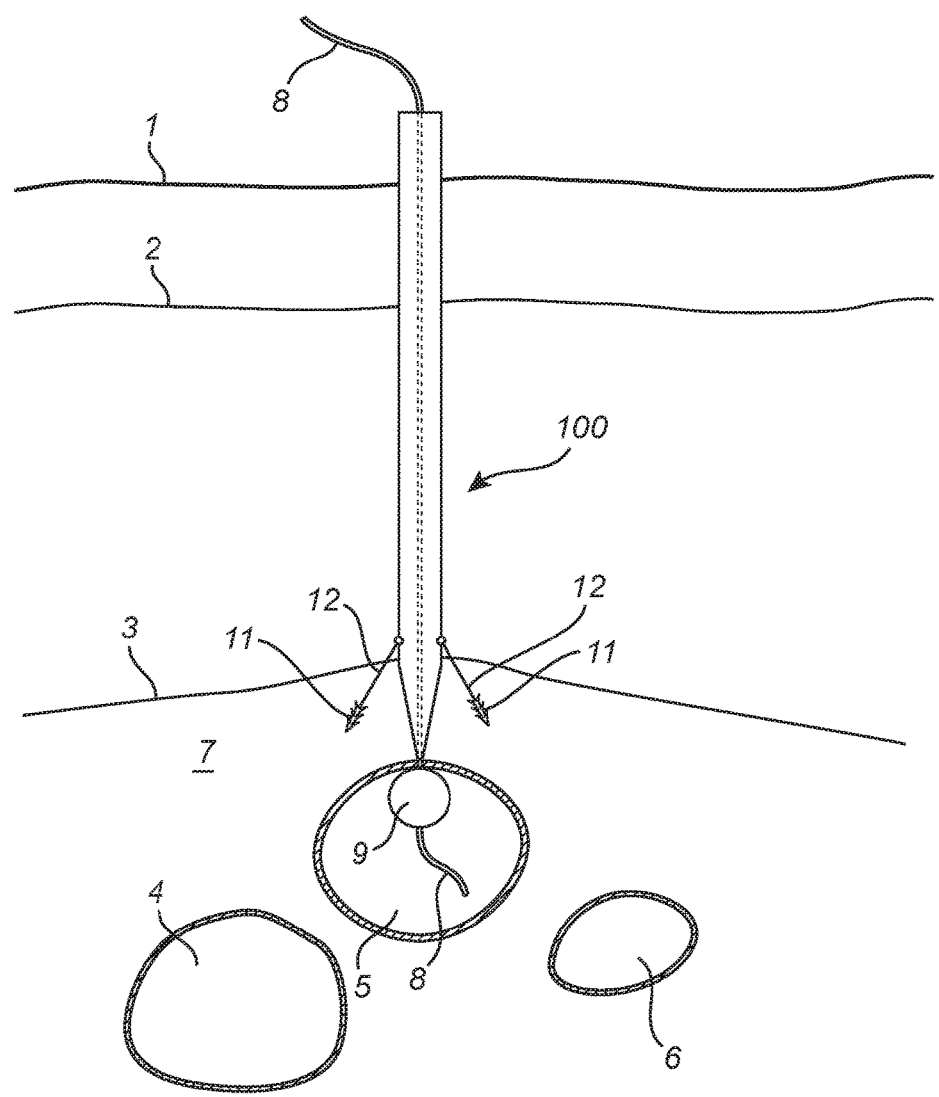
FIG. 1 schematically exemplifies a first embodiment of a vascular closure device according to a possible embodiment of the present disclosure.

The present disclosure will now be described more fully hereinafter with reference to the accompanying drawings, in which embodiments of the disclosure are shown. The present disclosure may, however, be embodied in many different forms and should not be construed as limited to the embodiments set forth herein; rather, these embodiments are provided for thoroughness and completeness, and fully convey the scope of the present disclosure to the skilled person. Like reference characters refer to like elements throughout.

Turning now to the drawings and to FIG. 1 in particular, the vascular closure device 100 is introduced percutaneously over a guide wire 8 into the blood vessel/artery 5, through the skin 1 and the fascia lata 2 of a patient. An optional anvil member 9 is arranged inside the blood vessel 5 to create a reference point to the engagement members 11 and/or for controlling bleeding. The engagement members 11 may then be placed and released through the vascular closure device 100 and may attach to tissue proximate to the blood vessel 5 and may involve the fascia membrane 3 (fascia iliacus), but not a wall of the blood vessel 5. The engagement members 11 may for example be pushed out of the vascular closure device 100 and into the fascia membrane 3 using deployment members provided as pusher rods 12 arranged in independent lumens provided with the vascular closure device 100, for example through a pusher assembly in a common lumen that simultaneously deploys all engagement members 11, through a spring-loaded mechanism or similar. The engagement members 11 are preferably connected with a single or a plurality of sutures as will be further elaborated below. In FIG. 1 there is further shown a femoral vein 4, a femoral nerve 6 and adjacent/interstitial tissues 7.

Figures 2A, 2B:
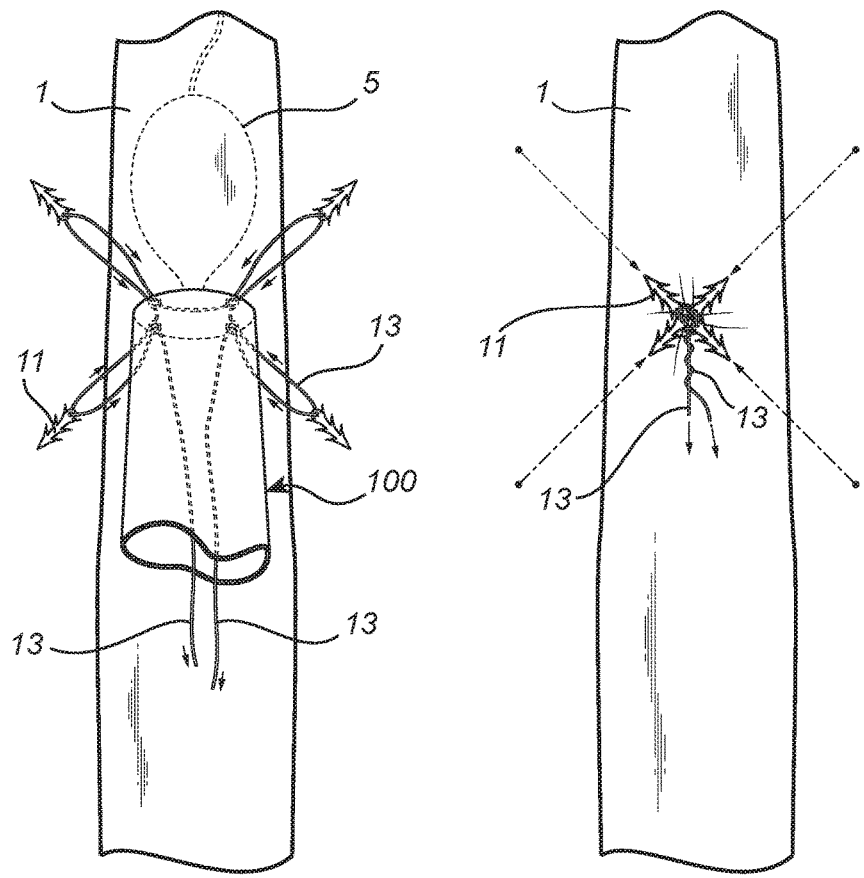
FIGS. 2A and 2B show a detailed view of the creation of a tissue lock using the vascular closure device.

With further reference to FIGS. 2A and 2B, the above-mentioned suture 13 may for example be routed through each of the engagement members 11 in sequence. In particular, one suture 13 may be looped through each of the engagement members 11 in sequence, or a separate suture 13 may be attached to each engagement member 11. The tissue, e.g. fascia membrane 3, is then pulled together with the suture 13 connected to the engagement members 11. When pulled together, the tissue/fascia membrane 3 is tightened towards the center and creates a tissue lock, thereby indirectly closing the artery 5. That is, a distance between the initial position of the engagement members 11 and a distance between the engagement members once the engagement members 11 have been moved towards each other is thereby reduced. When tightening the fascia membrane 3 the anvil member 9 may be removed from the artery 5.

Figures 2C, 2D:
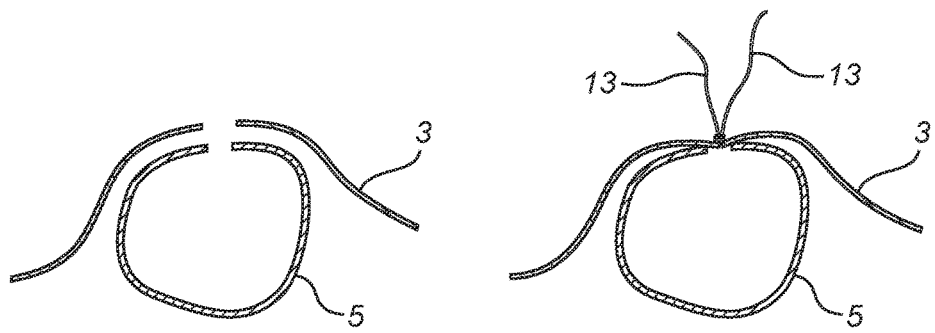
FIGS. 2C and 2D illustrate a closure sequence for treatment of an unwanted passage through a wall of a blood vessel.

Referring to FIGS. 2C and 2D, an embodiment of a closure sequence is shown whereby a passage through a wall of a vessel such as the blood vessel shown is treated such that leakage of blood from the interior volume of the blood vessel (not shown) is slowed or stopped to a clinically acceptable degree. As seen in FIG. 2C, a passage in the wall of the blood vessel, specifically, the femoral artery 5, is disposed in general alignment with a passage through the tissue layer disposed proximate to an outer surface of the femoral artery 5. For this particular exemplary embodiment, the tissue layer disposed outside of and proximate to the outer surface of the femoral artery 5 is the fascia iliacus 3. For purposes of this general discussion, the phrase "in general alignment" as applied to the respective passages may mean at least that an appropriately sized elongate device such as a catheter or sheath may pass through both passages without significant relative lateral displacement between the tissue 3 and artery 5. In addition, in some cases, the tissue layer 3 may be disposed sufficiently proximate the outside surface of the blood vessel 5 such that gathering and approximation of the tissue 3 which is disposed about the passage through the tissue 3 so as to close the passage through the tissue/fascia membrane 3 and form a tissue lock is sufficient to tighten and displace the closed gathered tissue/fascia membrane 3 against the outer surface of the artery 5 which is adjacent the passage through the artery 5 as shown in FIG. 2D. When the gathered tissue 3 has been displaced and deflected so as to be disposed against the passage of the artery 5 and wall of the artery 5 disposed about the passage in the artery 5, this mechanical approximation will typically be sufficient in order to achieve a clinically sufficient slowing or stoppage of blood leakage from the passage in the artery 5 in order to permit closure of an access site through the patient's skin 1 adjacent the passages. In some instances, an inner surface of the tissue layer 3 disposed proximate to the outer surface of the blood vessel 5 may be separated from the outer surface of the blood vessel in the region of the respective passages therethrough by a distance of up to about 10 mm, more specifically, up to about 5 mm.

Figure 3A:
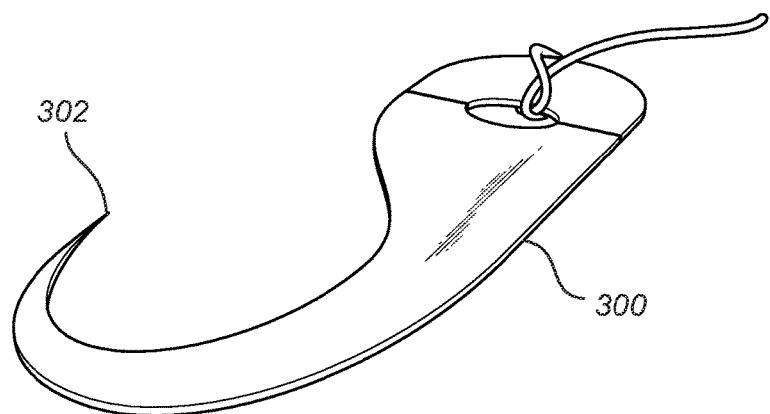
FIGS. 3A and 3B conceptually illustrate an engagement member, exemplified as an anchor element.
Figure 3B:
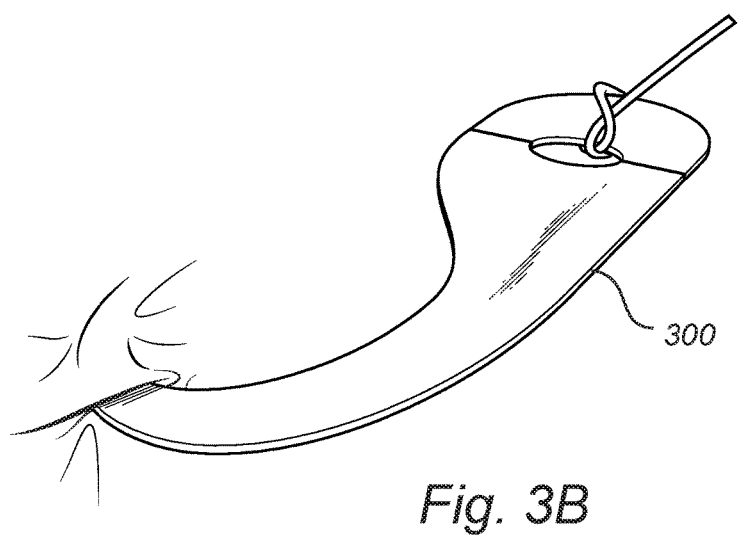

With further reference to FIGS. 3A and 3B, there is conceptually illustrated an engagement member, exemplified as an anchor element 300. In FIG. 3A, the anchor element 300 is shown as initially deployed, so that it slides easily in the direction away from a deployment point. Note that the deployment point may optionally be deflected toward the tissue/fascia membrane 3 to promote engagement. FIG. 3B shows the anchor element 300 after motion has been reversed toward the deployment point, and the anchor element 300 has embedded into the tissue/fascia membrane 3. That is, a tip 302 of the anchors element 300 is in one embodiment hook-shaped, so that it easily slides outward without engaging the tissue/fascia membrane 3. However, once the anchor element 300 is retracted, at least the tip 302 of the anchor element 300 is adapted to mechanically engage with the tissue/fascia membrane 3.

Figure 4A:
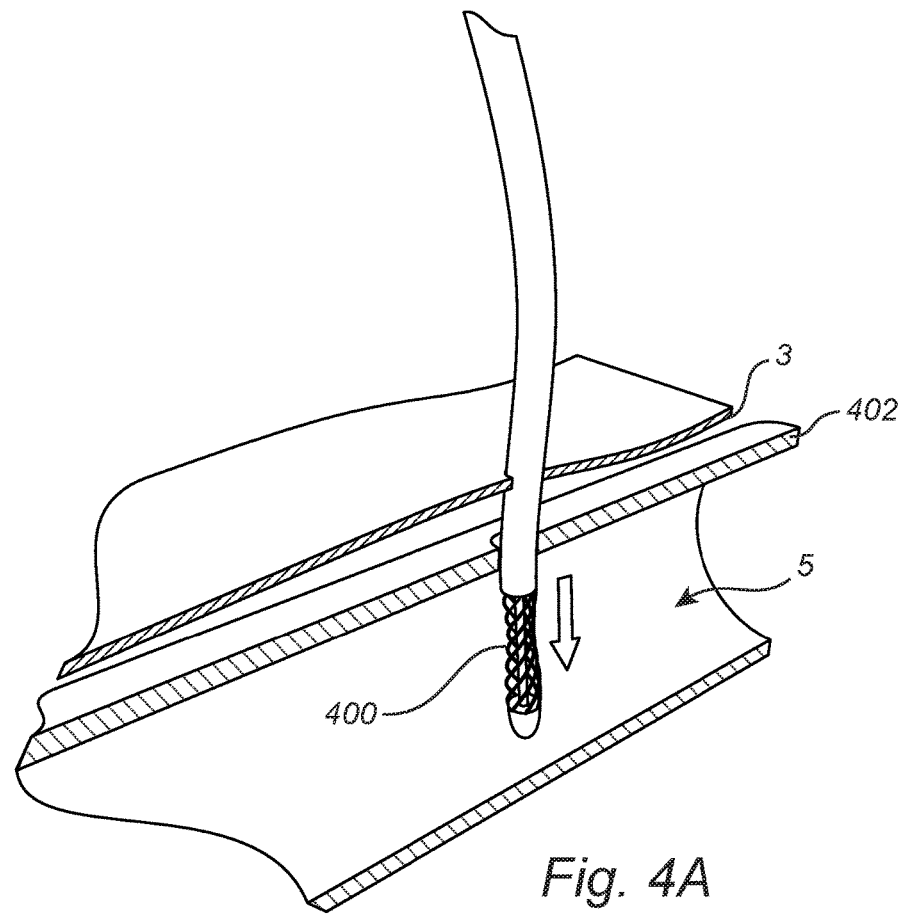
FIGS. 4A and 4B illustrate the operation of an anvil member that functions as a deployable positioning feature.
Figure 4B:
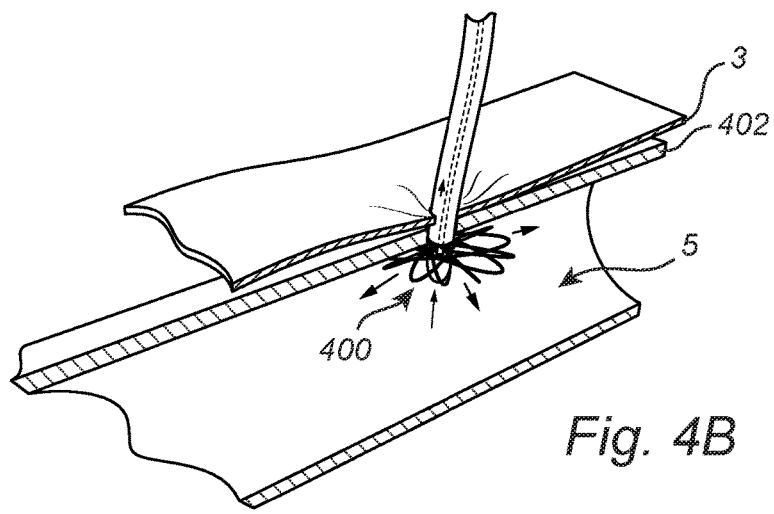

FIGS. 4A and 4B conceptually illustrate the operation of an anvil member exemplified as a deployable positioning feature 400. In FIG. 4A, deployable positioning feature 400 is inserted through the wall 402 and into the interior volume of the blood vessel, such as the femoral artery 5. The deployable positioning feature 400 is structured similar to an umbrella (using a mesh material), where the deployable positioning feature 400 in a radially collapsed form may be inserted into the artery 5. Once within the artery 5, with further reference to FIG. 4B, the deployable positioning feature 400 may be "unfolded" and radially expanded from the collapsed form such that a total surface area proximate to the longitudinal axis of the deployable positioning feature 400 is increased and thus may be retracted towards the interior wall of the artery 5. Accordingly, a reference point may be thereby established for further operation of the vascular closure device.

Figure 5A:
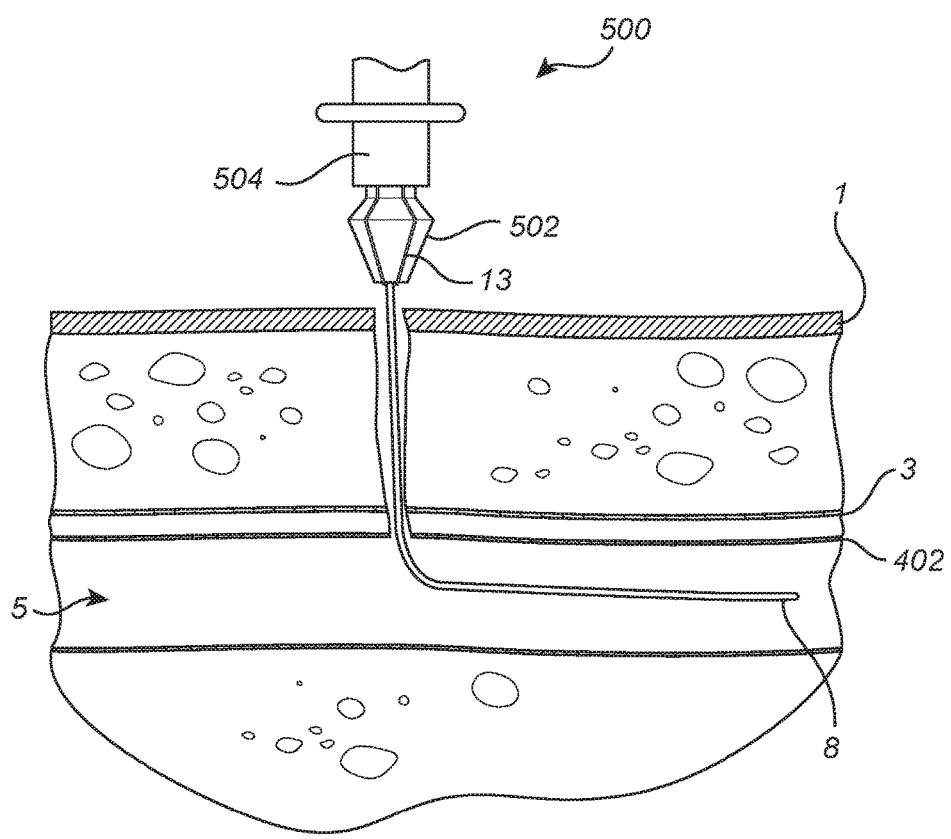
FIGS. 5A-5I show a sequence for operating an embodiment of the vascular closure device.
Figure 5B:
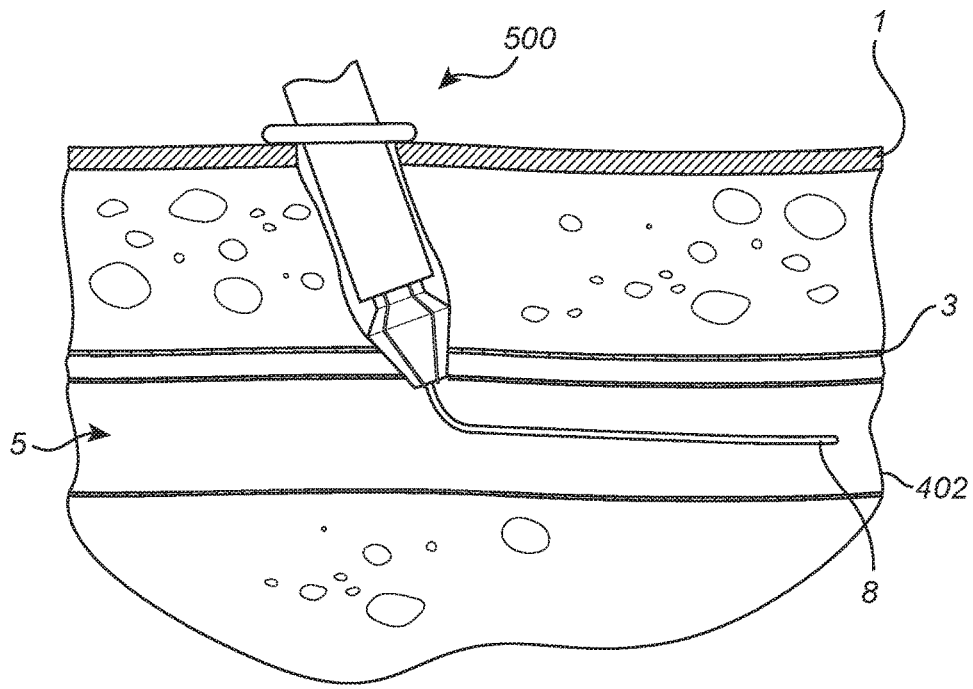
Figure 9A:
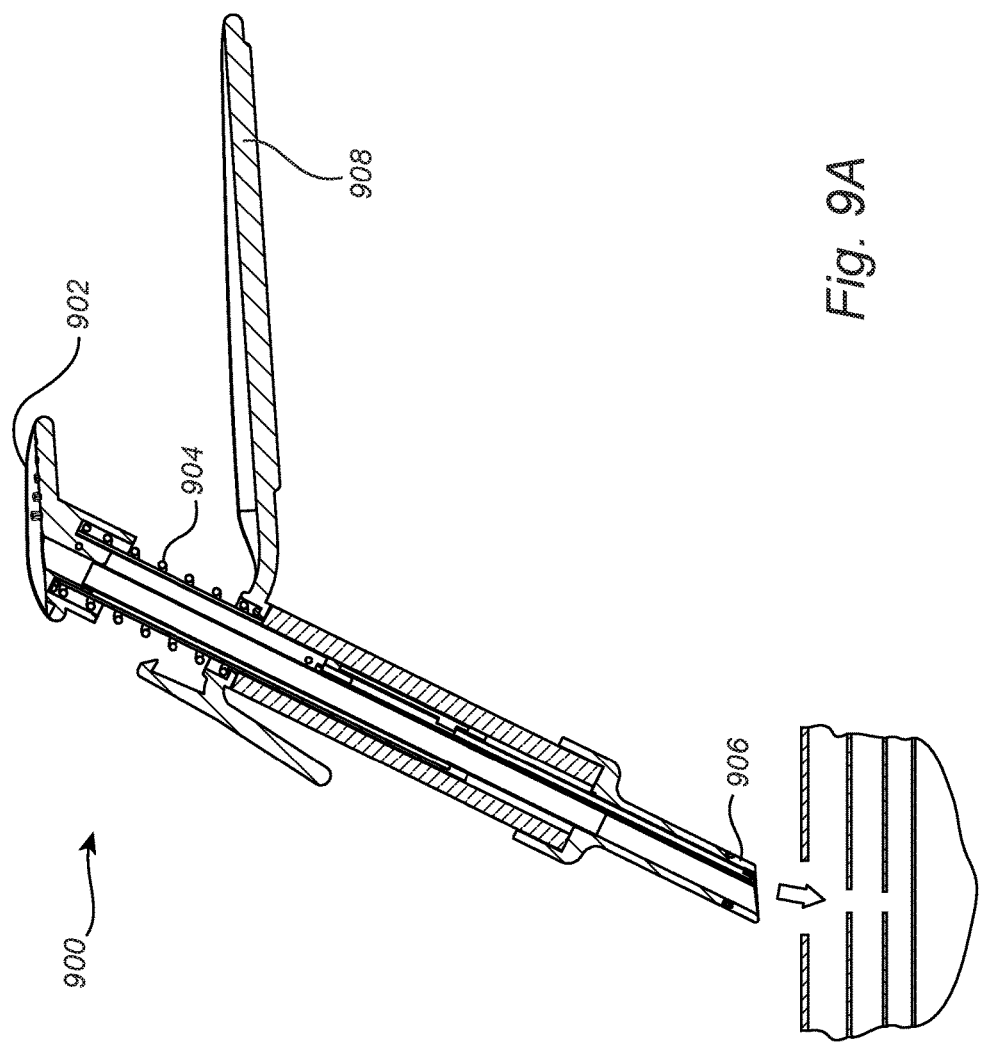
Figure 9C:
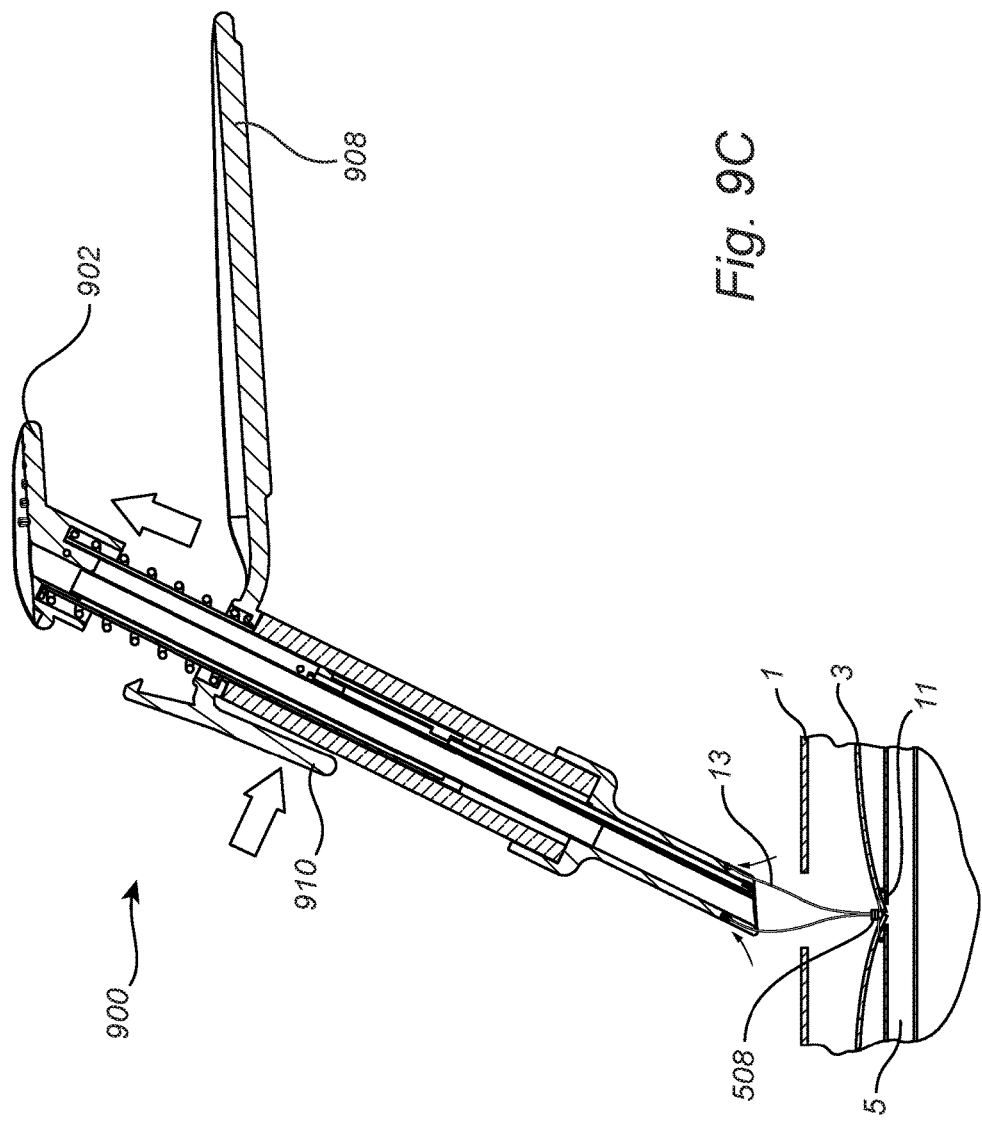
Figure 10:
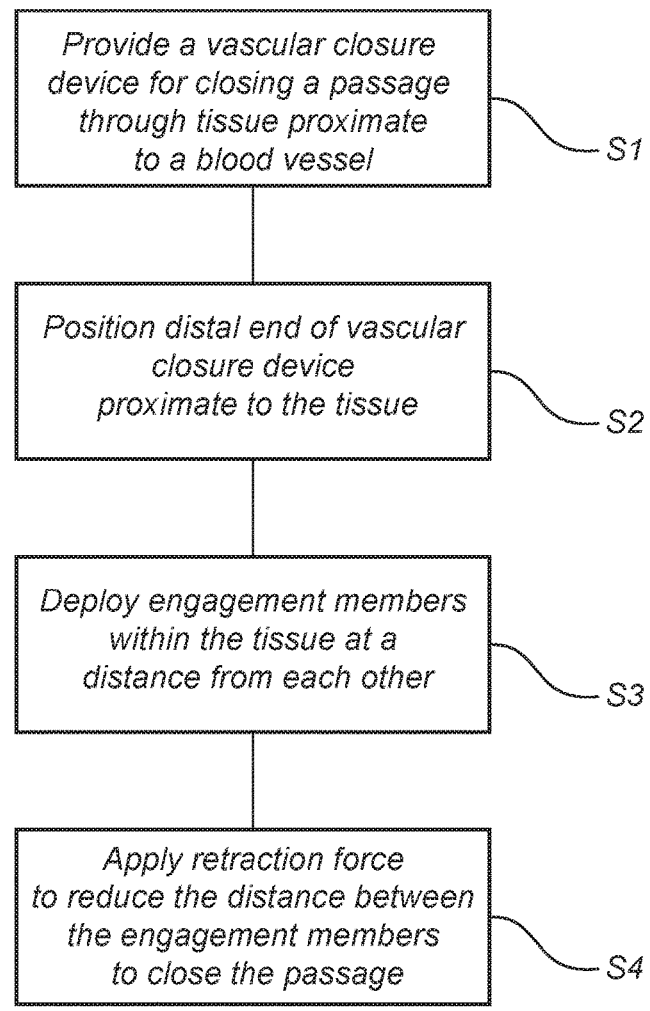
FIG. 10 is a flow chart showing the method steps for operating the vascular closure device according to the present disclosure.

FIGS. 5A-5I, in conjunction with FIG. 10, describe, in step-by-step fashion, the use of a vascular closure device 500 according to a second embodiment of the present disclosure. The first step, as shown in FIG. 5A, the vascular closure device 500 is provided, S1, in the deployment is to advance the vascular closure device 500 over e.g. a pre-existing guidewire 8 until the conical distal tip 502 (possibly provided with a conical nosecone) of an elongated housing 504 of the vascular closure device 500 is positioned, S2, and the pusher rods exit the housing proximate to the fascia membrane 3 above an outer surface of a wall the artery 5, as is shown in FIG. 5B. Optionally, the vascular closure device 500 may be aligned such that a longitudinal marker on the vascular closure device 500 (as will be further discussed below in relation to FIGS. 9A-9C, is approximately aligned with the longitudinal axis of the common artery 5 of the patient.

Figure 5C:
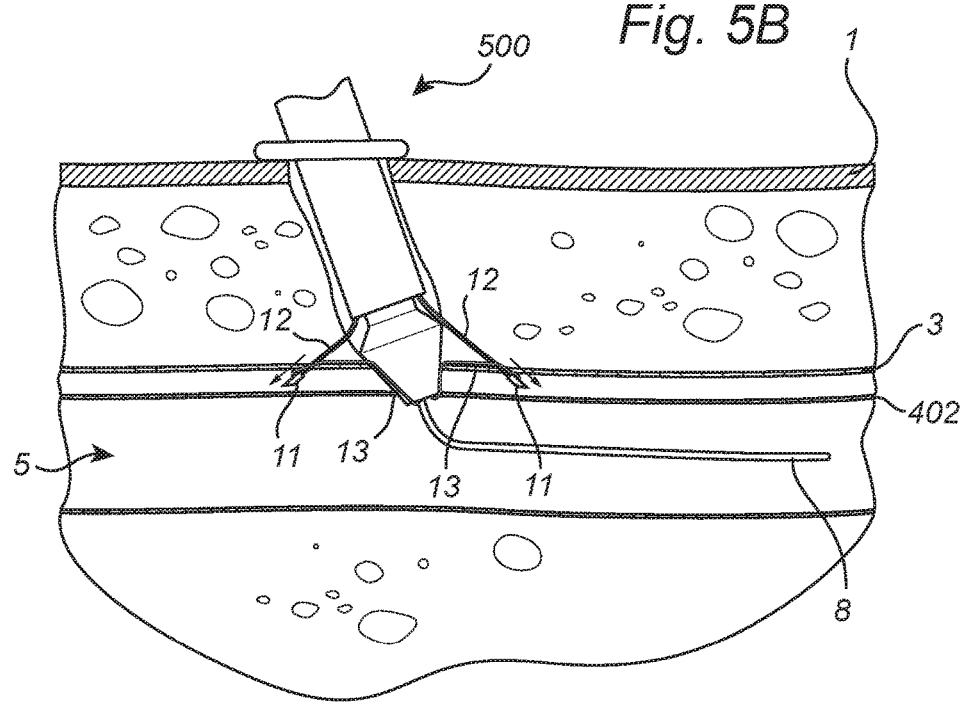
Figure 5D:
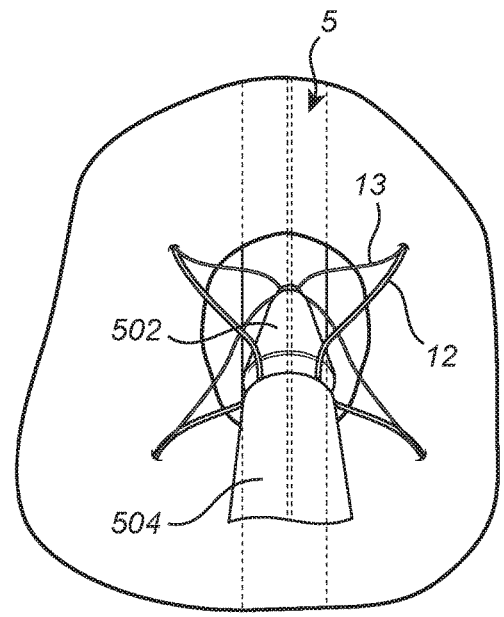

In this embodiment, one suture 13 for each engagement member 11 is initially routed through the center of the vascular closure device 500, out the distal tip, and up alongside the outer surface of the vascular closure device 500 and into the slot on the elongated housing 500 containing the undeployed engagement members 11. Thus, when the engagement members 11 are deployed, S3, as shown in FIG. 5C, the retraction member pulls the suture 13 that is routed from the distal tip 502 of the vascular closure device 500, up through the (pre-existing) hole in the fascia 3, and outward to the location of the engagement members 11, as shown in FIG. 5D.

Figure 5E:
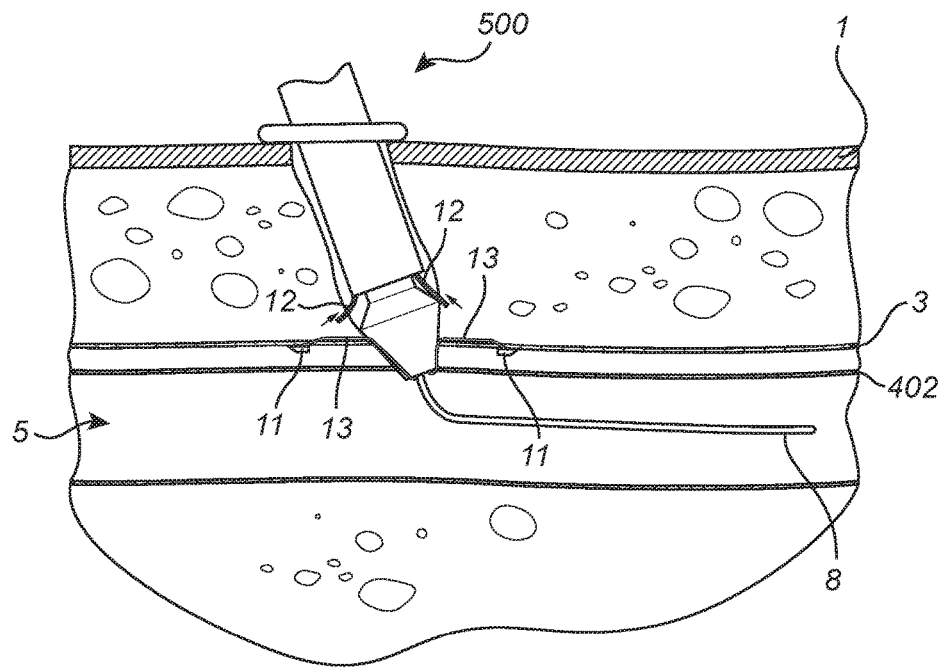

Once a retraction force is applied by the retraction member, S4, and the direction of is reversed, the engagement members 11 will mechanically engage the tissue/fascia membrane 3, as shown in FIG. 5E, and the pusher rods 12 (i.e. the deployment member) is withdrawn back into the slots, holes or lumens in the elongated housing 504 of the vascular closure device 500 from which they originally extended.

At this stage, a plurality of engagement members 11 (e.g. four, or any other number of engagement members, also an odd number of engagement members is possible) will be embedded in and secured to the tissue/fascia membrane 3 at locations circumferentially disposed around the passage to be closed in the tissue/fascia membrane 3 at positions on each side of the common femoral artery 5. In some cases, the engagement members 11 may be symmetrically disposed bilaterally on the medial and lateral sides of the common femoral artery 5. Each of the engagement members 11 has a suture 13 connected, and that suture 13 runs from the anchor, down through the hole in the fascia 3, and into the distal tip 502 of the vascular closure device 500.

Figure 5F:
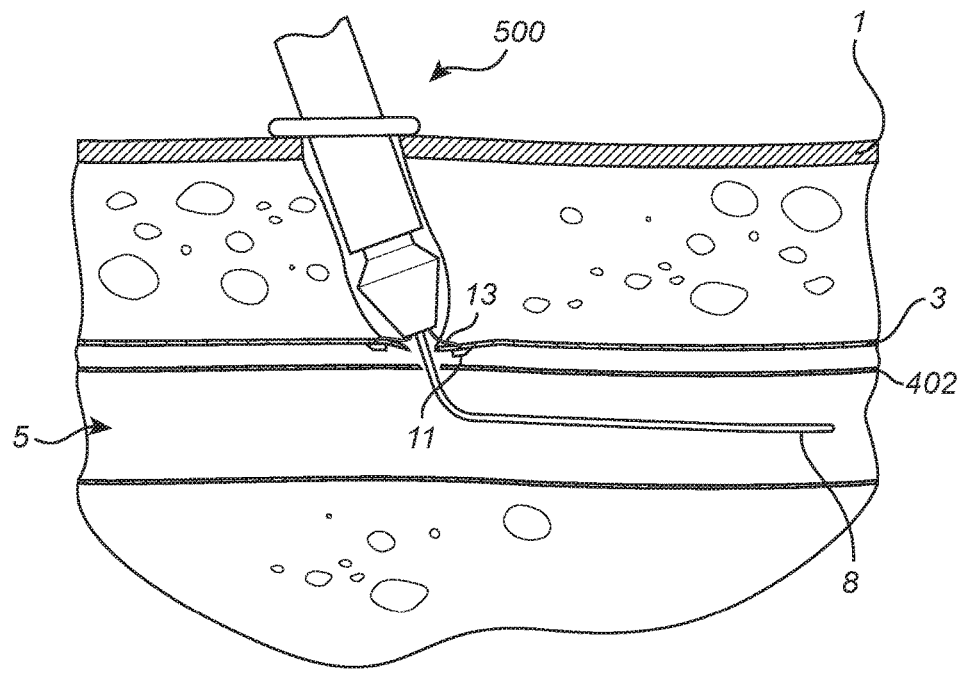

Next, initial tension is applied to the sutures to pull the engagement members 11 (and thus the fascia 3) toward the vascular closure device 500. Now the vascular closure device 500 may be slowly withdrawn until the distal tip 502 is at or just above the fascia layer 3, keeping tension on the sutures 13 to continue to pull the engagement members 11 together toward the distal tip 502 of the vascular closure device 500, thereby pulling all the engagement members 11 toward one point and closing the passage, as shown in FIG. 5F.

Figure 5G:
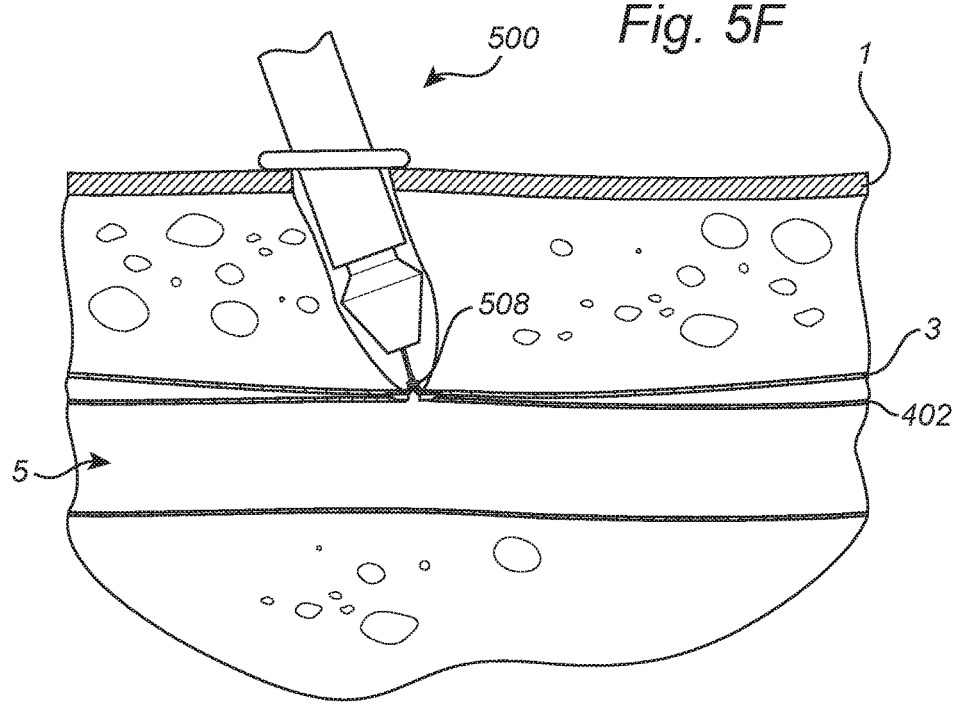

At this point, a locking member, such as a fixation ring 508 or sleeve, through which each of the sutures 13 passes, is deployed from the distal tip 502 of the vascular closure device 500, as shown in FIG. 5G. This fixation ring 508 compresses onto the bundle of multiple sutures 13 and locks them in place, thereby preventing the fascia membrane 3 and thus the passage from reopening, thereby indirectly closing the artery 5. Furthermore, as a desired level of hemostasis is achieved, also the guidewire 8 may be removed while holding tension on the sutures 13. The guidewire 8 may be for example routed alongside of, but not through, the fixation ring 508. This may allow the sutures 13 to be fully retracted and the fixation ring 508 to be deployed to lock the sutures 13 in place without removing the guidewire 8.

This fixation ring 508 may be spring-like, held open only by its mounting on the vascular closure device 500, such that it automatically closes down on the sutures 13 after being deployed from the vascular closure device 500. Alternatively, this locking ring function could be accomplished by another suture loop with a pre-tied knot that is cinched down to anchor the other sutures that are connected to the anchors. In yet another embodiment of the fixation ring 508 could be a fusion mechanism that uses heat and/or pressure to fuse the sutures together to provide fixation. In yet another embodiment a fixation ring could be a small tube through which sutures are initially and slidably routed, said tube being compressed by a mechanism in the housing to trap sutures and create fixation.

Figure 5H:
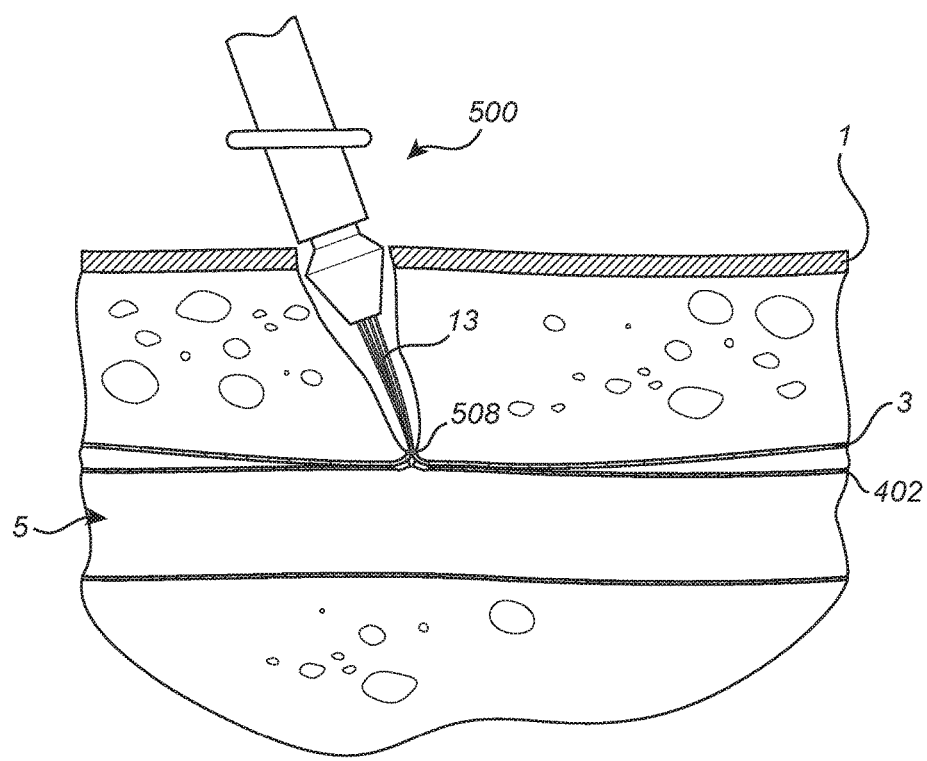
Figure 5L:
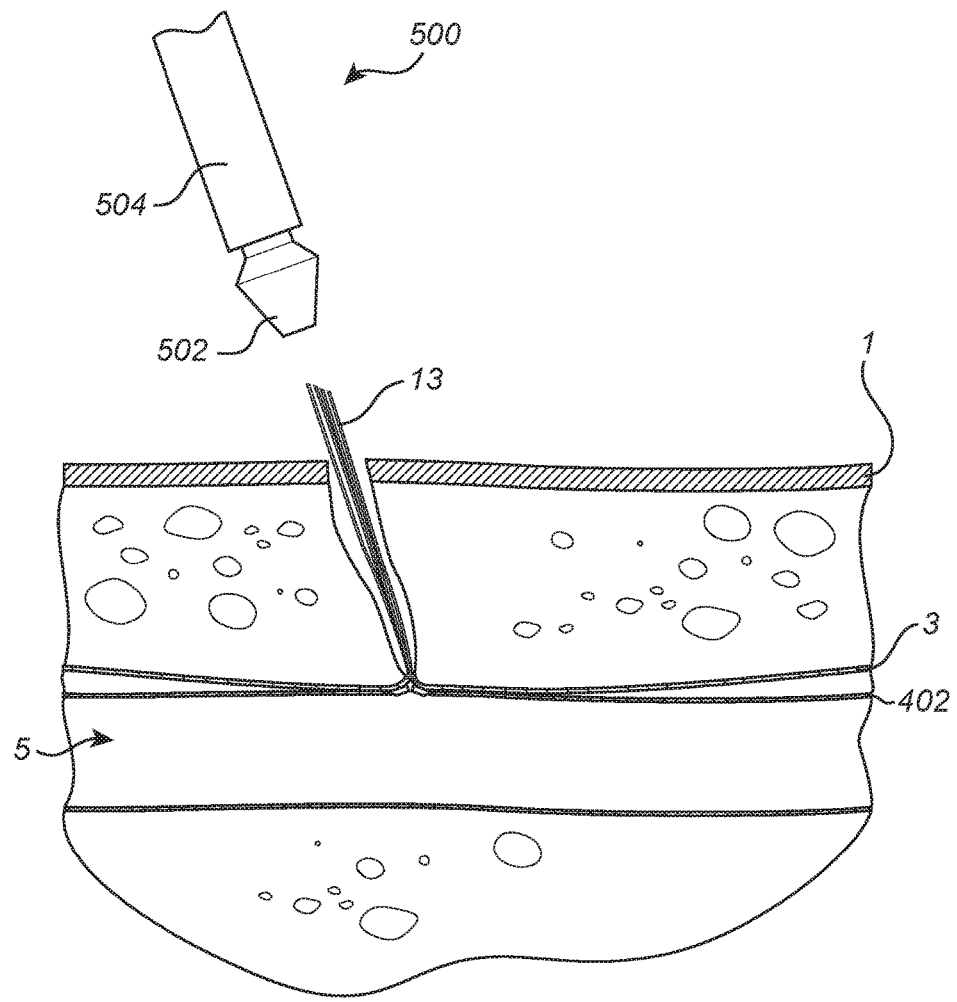

The vascular closure device 500 removal may be continued at this stage, as the passage closure is complete, as shown in FIG. 5H. Optionally, once the sutures 13 are fixed in place, a mechanism within the vascular closure device 500 handle may be activated to cut the sutures just above the fixation ring/zone. Alternatively, the sutures 13 may be left at this stage and trimmed at the skin surface by the operator, as shown in FIG. 5I. The vascular closure device 500 is now fully removed.

Figure 6A:
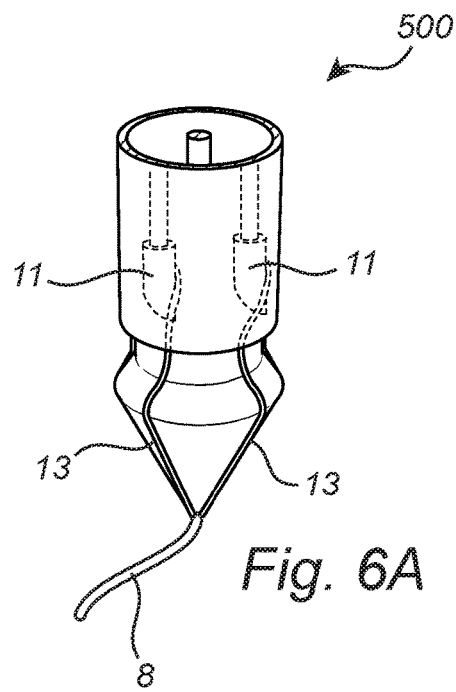
FIGS. 6A-6F illustrate a perspective view of operating the vascular closure device as shown in FIGS. 5A-5I.
Figure 6B:
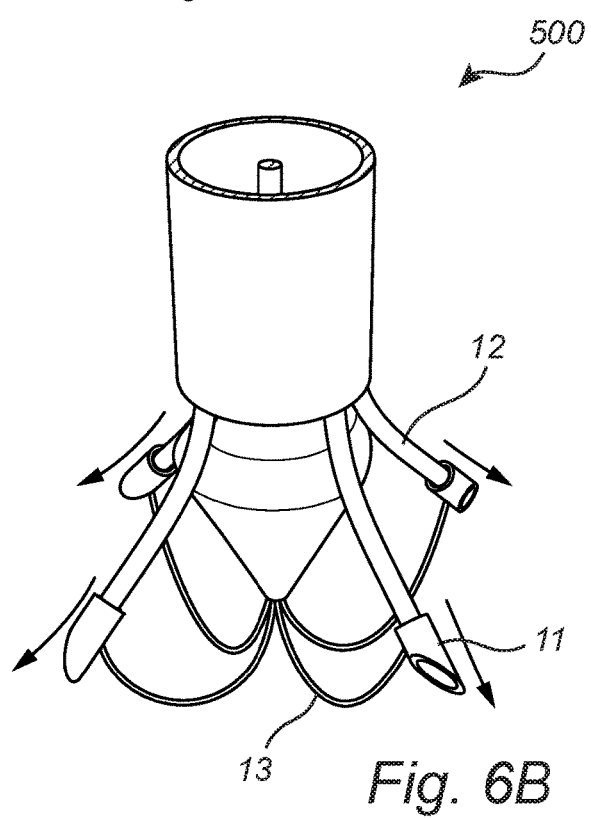
Figure 6C:
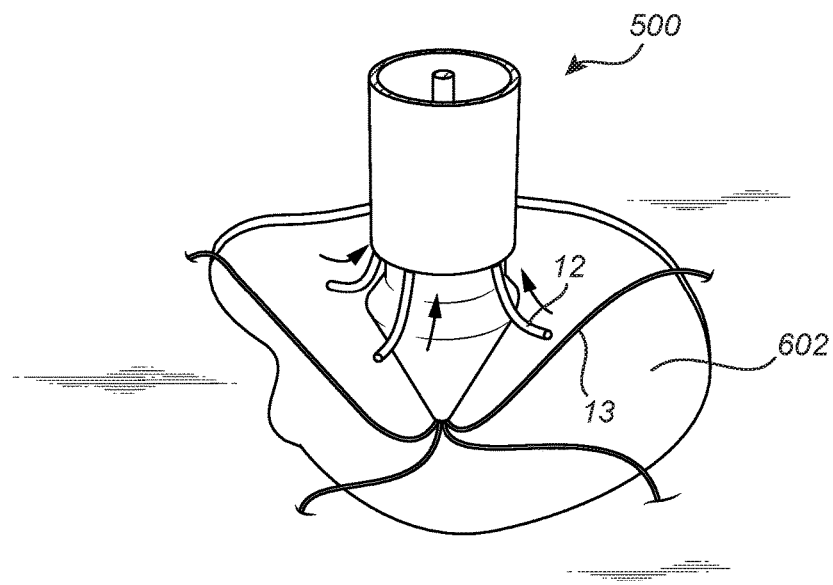
Figure 6D:
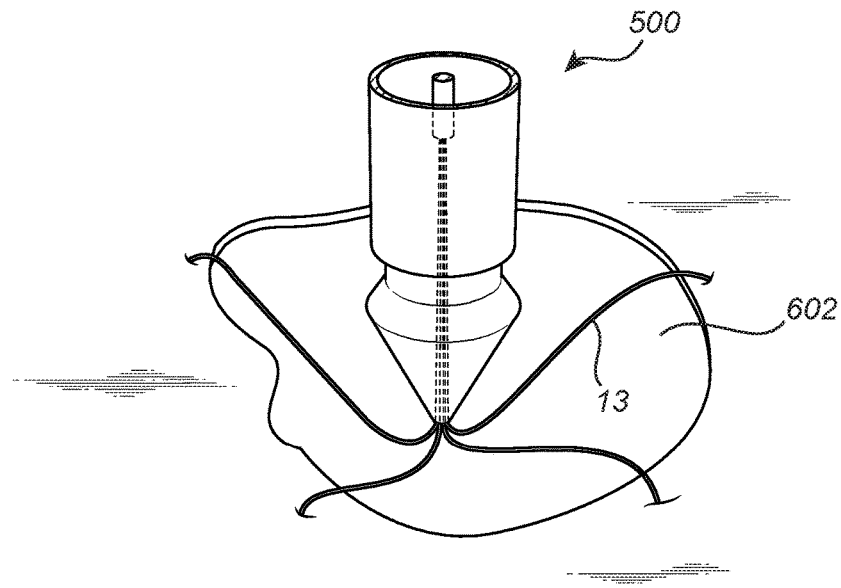
Figure 6E:
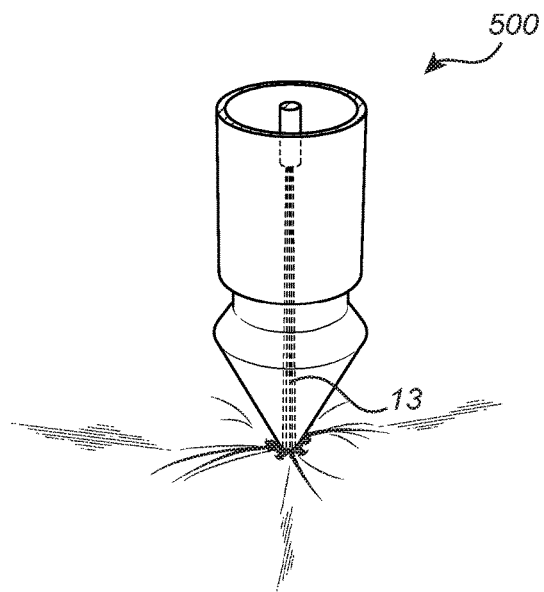
Figure 6F:
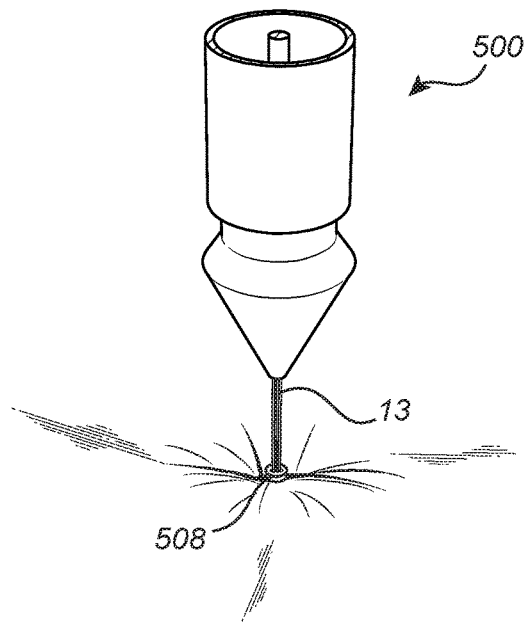

An alternative view of the disclosure is shown in FIGS. 6A-6F. Note that the fascia membrane 3 is omitted in FIGS. 6A and 6B for clarity in these images. FIG. 6A, the vascular closure device 500 advanced over guidewire 8 until tapered distal tip 502 is positioned such that deployment members (e.g. pusher rods 12) exit the housing proximal to the fascia layer above the artery 5. In FIG. 6B, engagement members 11 are deployed from the elongated housing 504 of the vascular closure device 500, pulling along the pre-attached sutures 13 routed through the distal tip 502 of the vascular closure device 500. In FIG. 6C, motion is reversed using a retraction member (as will be further elaborated below), thereby embedding the engagement members 11 into the tissue/fascia membrane 3, for example according to a pre-determined pattern surrounding the passage 602 through the tissue/fascia membrane 3. The engagement members 11 are then released from the deployment member. In FIG. 6D, the engagement members 11 are in place with sutures 13 attached and the deployment members (e.g. pusher rods 12) are retracted using the predetermined retraction force. In FIG. 6E, the vascular closure device 500 is partially withdrawn until the distal tip 502 is just above fascia membrane 3, whereby suture tension is applied to pull the engagement members 11 together and to close the passage 602, i.e. such that a diameter of the passage 602 is reduced. In FIG. 6F, sutures 13 are fixated, and the vascular closure device 500 is withdrawn.

Optionally, a hemostasis member (not explicitly shown in these images) may be added to the distal tip 502 of the vascular closure device 500. This hemostasis member may be initially placed inside the artery 5 as the vascular closure device 500 is advanced to abut the fascia membrane 3, and the hemostasis device activated to prevent bleeding from the artery 5 during use of the vascular closure device 500. As the engagement members 11 are being brought together during initial retraction of the vascular closure device 500, the hemostasis member may be deactivated and withdrawn. One example of a hemostasis member is an inflatable compliant balloon. Furthermore, a hollow lumen may optionally be left in the center of the elongated housing 506, through which a dilator or cannula may be placed to facilitate initial insertion of the vascular closure device 500. This dilator may be slowly removed as an aid to maintaining hemostasis during the tightening of the sutures 13.

Figure 7C:
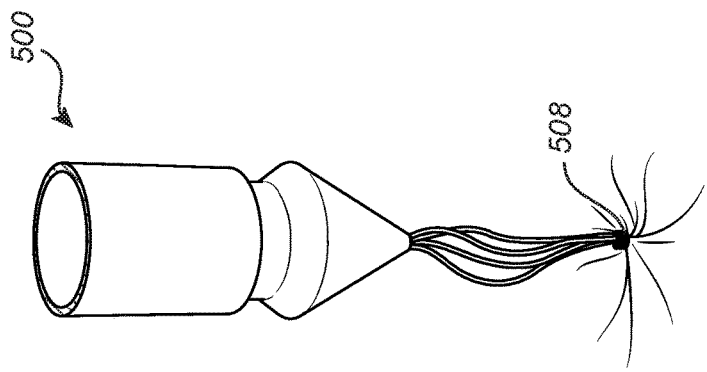
FIGS. 7A-7C conceptually illustrate the application of a locking member, provided in the form of a preloaded coil arranged to clench the suture.
Figure 7B:
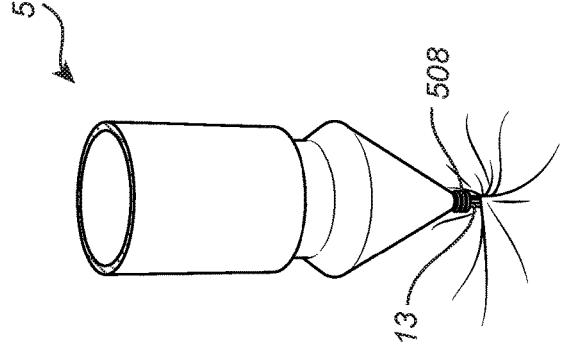
Figure 7A:
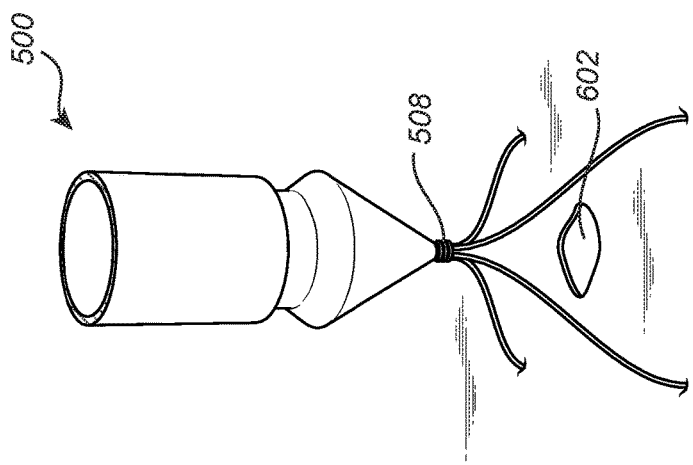

FIGS. 7A-7C provide a detailed view for the application of a locking member or fixing ring, here provided in the form of a preloaded locking coil 508 arranged to clench the suture 13. In FIG. 7A, the locking coil 508 is depicted in its initial position, stretched onto the outer surface of a lumen extending from the distal end of a portion of housing 504, with sutures 13 passing through this lumen to each of the engagement members 11, which have been deployed to engage the tissue/fascia membrane 3. In FIG. 7B, the retraction member (for example implemented using a mechanism for applying the above-mentioned retraction force) has been used to apply tension to the sutures 13, resulting in a reduction of distance between the engagement members 13, thereby closing the passage 602 in the tissue/fascia membrane 3. The suture retention coil 508 has been pushed off the lumen noted above, and has contracted to grasp and fixate the sutures 13 to retain the engagement members 11 in their proximate positions. In FIG. 7C, the vascular closure device 500 has been withdrawn and the locking coil 508 has retained the engagement members 11 in their proximate positions, thereby enabling all tension to be released from the suture 13 in preparation for complete removal of the vascular closure device 500, suture trimming just below the skin level, and completion of the closure procedure.

FIGS. 8A-8C illustrate the operation of an engagement member 11, provided as a tube shaped element has been inclined or cut at one end portion. The tube shaped element may, for example, be formed from a cut hypotube 800. In FIG. 8A, the hypotube 800 is shown mounted on the tip of the deployment member, here illustrated as arranged at the pushrod 12, and the suture 13 is here shown attached to a location in the middle region of the hypotube 800. The sharp/cut end of the hypotube 800 is about to penetrate the fascia membrane 3. In FIG. 8B, the hypotube 800 has penetrated the fascia membrane 3, and the pushrod 12 has been retracted leaving only the hypotube 800 and the attached suture 13 in position. Tension has been applied to the suture 13, and since the suture 13 is attached to the hypotube 800 in the middle region of one side, the hypotube 800 is in the process of rotating approximately 90° as it comes to bear on the underside of the fascia membrane 3. In FIG. 8C, the rotation process is complete and, as tension in the suture 13 has increased, the hypotube 800 has come into full contact with the fascia membrane 3 with contact occurring along the longitudinal axis of the hypotube 800, thereby increasing the contact area and reducing the likelihood that the hypotube 800 could simply pull back out of the fascia membrane 3 through the hole created when it originally penetrated the fascia membrane 3. In some cases, the hypotube 800 may be said to be mechanically captured by the fascia membrane 3 when in such full contact with fascia after the rotation process is complete as shown in FIG. 8C.

FIGS. 9A-9C illustrate a cross section of a further embodiment of a vascular closure 900. FIG. 9A shows the device in its initial configuration. The pushrods 12, i.e. engagement members, and suture 13 are contained within the device (not directly visible in FIG. 9A). A thumb button 902 is in FIG. 9A shown as not yet depressed, and an underlying coil spring 904 is in an extended position. The engagement members 11 are seen in their initial position nestled into the distal end 906 of the housing at the distal end of the engagement members 11. The vascular closure device 900 further comprises a device-positioning member, in the form of an elongated handle 908, to be aligned with an expected direction of the blood vessel.

FIG. 9B shows the vascular closure device 900 after the engagement members 11 have been deployed. The thumb button 902 has been depressed, thereby compressing the underlying coil spring 904, and engaging a top clip 910 to retain it in place. The pushrods 12 are visible in their extended position, with the engagement members 11 still attached to the distal tips. FIG. 9C shows the vascular closure device 900 in a completion state, where the engaging clip 910 has been released, whereby the coil spring 904 will move back towards its initial position. In moving back to its initial position, a retraction force will be applied (using retraction members, not explicitly shown), whereby the sutures 13 are "drawn" back into the vascular closure device 900. As discussed above, once the sutures 13 are drawn back into the vascular closure device 900, the distance between the engagement members 11 will be reduced, consequently reducing the diameter of the passage through the tissue/fascia membrane 3, indirectly forming the tissue look. Once the sutures have been completely retracted (based on the predetermined retraction force applied by means of the coil spring 904), the locking member, such as the fixation ring 508 is positioned to secure the sutures 13 in the retracted state.

The prior description of the vascular closure device has focused on its initial use to close a vascular access, but in the event this initial use does not provide clinically acceptable hemostasis, it may be possible in some embodiments to use one or more additional vascular closure devices discussed herein to deploy additional engagement members and further support the approximation of the tissue to improve hemostasis to a clinically acceptable level.

Although the figures may show a sequence, the order of the steps may differ from what is depicted. Specifically, the anchor hook characteristic is shown much larger than actual for illustration purposes. In addition, two or more steps may be performed concurrently or with partial concurrence. Such variation may depend on the structural elements used and on designer choice. All such variations are within the scope of the disclosure. Additionally, even though the present disclosure has been described with reference to specific exemplifying embodiments thereof, many different alterations, modifications and the like will become apparent for those skilled in the art. In addition, any suitable feature, dimension or material of any particular vascular closure device embodiment discussed herein may be used or otherwise combined with any of the other vascular closure device embodiments discussed herein.

Furthermore, variations to the disclosed embodiments can be understood and effected by the skilled addressee in practicing the present disclosure, from a study of the drawings, the disclosure, and the appended claims. Furthermore, in the claims, the word "comprising" does not exclude other elements or steps, and the indefinite article "a" or "an" does not exclude a plurality.

The invention claimed is:

1. A vascular closure device for treating a passage in a blood vessel by closing a passage through tissue proximate to the blood vessel, the vascular closure device comprising:

an elongated housing having a proximal end, a distal end, and a distal section;

a plurality of engagement members which are each adapted to be secured to tissue upon deployment into tissue;

a plurality of deployment members adapted to extend the engagement members from the distal section of the elongated housing in a distal and radially outward direction, each of the deployment members being adapted to deploy at least one of the engagement members by pushing the at least one engagement member in a distal and radially outward direction into the tissue proximate to the blood vessel such that the engagement members are secured to the tissue proximate to the blood vessel and disposed at a distance from each other in engaged contact with said tissue, without engaging a wall portion of the blood vessel;

a plurality of elongate flexible tension elements, each tension element being secured to a separate engagement member and routed through a center of the vascular closure device and out of a distal tip thereof; and a retraction member coupled in operative arrangement with the tension elements and adapted to apply axial tension to the tension elements and reduce the distance between the engagement members to a radially retracted state to close the passage in the tissue proximate to the blood vessel.

2. The vascular closure device according to claim 1, further comprising a locking member adapted to secure the tension elements relative to each other in the retracted state thereby creating a tissue lock.

3. The vascular closure device according to claim 1, wherein the deployment members are adapted to deploy the engagement members into the tissue proximate to the blood vessel at a predetermined radial distance from the distal end of the vascular closure device.

4. The vascular closure device according to claim 1, wherein the engagement members are adapted to mechanically capture the tissue proximate to the blood vessel.

5. The vascular closure device according to claim 1, wherein the engagement members are adapted to rotate, pivot or expand once in engaged connection with the tissue.

6. The vascular closure device according to claim 5, wherein the engagement members each comprise a hypotube section having an included sharpened end portion.

7. The vascular closure device according to claim 1, wherein the engagement members are adapted to engage with a fascia membrane of said tissue.

8. The vascular closure device according to claim 1, wherein the elongate flexible tension members comprise sutures secured to the engagement members, and wherein the retraction member is adapted to retract the sutures toward a common position adjacent a surface of the tissue proximate to the blood vessel in order to reduce the distance between the engagement members and associated tissue respectively engaged therewith.

9. The vascular closure device according to claim 8, wherein the sutures are formed of a biodegradable or bio-absorbable material.

10. The vascular closure device according to claim 1, wherein the engagement members are formed of a biodegradable or bio-absorbable material.

11. The vascular closure device according to claim 1, wherein the elongated housing further comprises a guidewire lumen allowing the vascular closure device to be advanced over a guidewire.

12. The vascular closure device according to claim 1, wherein the deployment members further comprise a spring-loaded portion adapted to project the engagement members into the tissue.

13. The vascular closure device according to claim 1, wherein the retraction member is adapted to apply a predetermined amount of force to the tension elements to thereby reduce the distance between the engagement members which have been secured to the tissue.

14. The vascular closure device according to claim 1, further comprising a tapered nosecone arranged at the distal end of the elongated housing.

15. A vascular closure device for closing a passage through tissue proximate to a blood vessel, the vascular closure device comprising:

an elongated housing having a proximal end and a distal end, the distal end adapted to be proximate the tissue;

a first engagement member and a second engagement member which are releasably arranged with the elongated housing;

a plurality of deployment members arranged with the elongated housing and adapted to deploy the first engagement member and the second engagement member by pushing the first engagement member and second engagement member in a distal and radially outward direction into the tissue proximate to the blood vessel at a distance from each other in engaged contact with said tissue, without engaging a wall portion of the blood vessel;

a plurality of tension elements, each tension element being secured to a separate engagement member and routed through a center of the vascular closure device and out of a distal tip thereof; and a retraction member which is arranged with the elongated housing, which is coupled in operative arrangement with the tension elements, which is adapted to apply axial tension to the tension elements, and which is adapted to reduce the distance between the first and the second engagement member to close said passage.

16. The vascular closure device according to claim 15, wherein the first and the second engagement member are adapted to mechanically capture the tissue.

17. The vascular closure device according to claim 15, wherein the first and the second engagement member are adapted to engage with a fascia membrane of said tissue.

18. The vascular closure device according to claim 15, wherein each of the tension elements comprise a suture and wherein the retraction member is adapted to retract the sutures to reduce the distance between the first engagement member and the second engagement member.

19. The vascular closure device according to claim 18, further comprising a locking member arranged with the elongated housing and adapted to maintain the sutures in a retracted state, thereby creating a tissue lock.

* * * * *